United States Patent [19]

Boltze et al.

[11] Patent Number: 4,564,613

[45] Date of Patent: Jan. 14, 1986

[54] PYRIDOINDOLE DERIVATIVES, COMPOSITIONS AND USE

[75] Inventors: Karl-Heinz Boltze, Borod; Margaret A. Davies, Cologne; Bodo Junge, Wuppertal; Teunis Schuurman, Overath; Jörg Traber, Lohmar, all of Fed. Rep. of Germany

[73] Assignee: Troponwerke GmbH & Co., Cologne, Fed. Rep. of Germany

[21] Appl. No.: 651,001

[22] Filed: Sep. 14, 1984

[30] Foreign Application Priority Data

Sep. 21, 1983 [DE] Fed. Rep. of Germany ....... 3333994

[51] Int. Cl.$^4$ .................. A61K 31/44; A61K 31/535; C07D 471/14; C07D 471/04
[52] U.S. Cl. .................................. 514/222; 514/227; 514/230; 514/238; 514/239; 514/252; 514/278; 514/287; 514/292; 544/58.6; 544/61; 544/70; 544/78; 544/126; 544/357; 544/361; 546/15; 546/64; 546/84; 546/86; 546/87
[58] Field of Search .................. 544/58.6, 61, 70, 78, 544/126, 357, 361; 546/15, 64, 84, 86, 87; 514/222, 227, 230, 238, 239, 252, 278, 287, 292

[56] References Cited

PUBLICATIONS

R. C. Elderfield, "Heterocyclic Compounds", vol. 3, 1952, John Wiley & Sons, N.Y., pp. 208, 209.
Chemical Abstracts, vol. 86, No. 25, Jun. 20, 1977, p. 611, col. 2, Abstract No. 189,902k, "Pyridoindole Derivatives", R. Tachikawa.
Chemical Abstracts, vol. 84, No. 11, Mar. 15, 1976, p. 440, col. 1, Abstract No. 74,140b, "Bischler-Napieralski Reactions . . . ", S. Naruto.

Primary Examiner—Robert W. Ramsuer
Attorney, Agent, or Firm—Sprung, Horn, Kramer & Woods

[57] ABSTRACT

Pyridoindoles of the formula

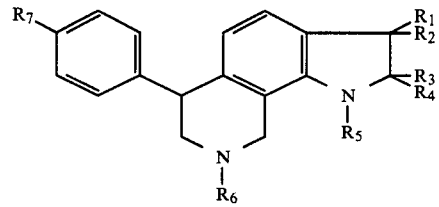

in which $R_1$ represents hydrogen or $C_1$–$C_4$-alkyl, which is optionally substituted by the radical

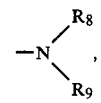

$R_2$ and $R_3$ represent H or form a bond, or
$R_1$ and $R_2$ together represent O, —O—CH$_2$—CH$_2$—O— or —S—CH$_2$—CH$_2$—S—,
$R_4$ represents H or the

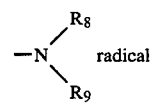 radical or
$R_3$ and $R_4$ represent O, or
$R_1$ and $R_4$ are members of an N-containing six-membered ring and
$R_8$ and $R_9$ represent H or $C_1$–$C_4$-alkyl, or optionally form, with the N atom, a heterocyclic 5-membered or 6-membered ring, which can optionally also contain a further hetero-atom from the series comprising N, O or S,
$R_5$ represents H, $C_1$–$C_4$-alkyl or the group

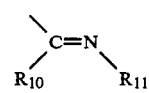

or
$R_5$ and $R_3$ form a bond, and
$R_{10}$ and $R_{11}$ represent $C_1$–$C_4$-alkyl or are members of an N-containing 5-membered or 6-membered ring,
$R_6$ represents H or $C_1$–$C_4$-alkyl and
$R_7$ represents halogen, or acid addition salts thereof, which are active on the central nervous system. Novel intermediates are also shown.

10 Claims, No Drawings

PYRIDOINDOLE DERIVATIVES, COMPOSITIONS AND USE

The present invention relates to new pyridoindole derivatives and acid addition salts thereof, processes for their preparation and their use in combating diseases, in particular their use for the treatment of diseases of the central nervous system.

The invention relates to pyrodoindoles of the general formula I

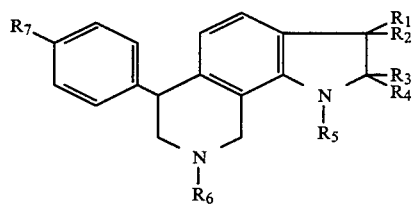

in which
R$_1$ represents hydrogen or straight-chain or branched C$_1$–C$_4$-alkyl, which is optionally substituted by the radical

R$_2$ and R$_3$ represent H or form a bond, or
R$_1$ and R$_2$ together represent oxygen, —O—CH$_2$—CH$_2$—O— or —S—CH$_2$—CH$_2$—S—,
R$_4$ represents H or a

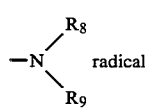 radical or
R$_3$ and R$_4$ represent oxygen, or
R$_1$ and R$_4$ are members of an N-containing six-membered ring and
R$_8$ and R$_9$ represent H or C$_1$–C$_4$-alkyl, or optionally form, with the N atom, a heterocyclic 5-membered or 6-membered ring, which can optionally also contain a further hetero-atom from the series comprising N, O or S,
R$_5$ represents H, C$_1$–C$_4$-alkyl or the group

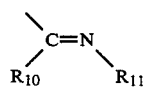

or
R$_5$ and R$_3$ form a bond, and
R$_{10}$ and R$_{11}$ represent C$_1$–C$_4$-alkyl or are members of an N-containing 5-membered or 6-membered ring,
R$_6$ represents H or C$_1$–C$_4$-alkyl and
R$_7$ represents H or halogen, in particular F, Cl or Br.

The invention extends to the racemic mixture as well as to the individual enantiomers of the compounds of the formula I. The enantiomers can be prepared from the racemates by conventional methods, for example by fractional crystallization of diastereomeric salts with optically active acids or by column chromatography on optically active carrier materials.

It has furthermore been found that the compounds of the general formula I are obtained when compounds of the general formula II

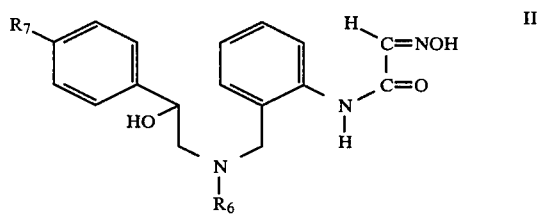

in which
R$_6$ and R$_7$ have the abovementioned meaning, are subjected to a double-cyclization reaction in the presence of a dehydrating agent. Isatins of the general formula Ia are thus obtained.

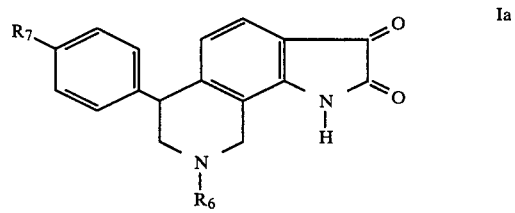

Compounds of the formula Ia are also obtained when compounds of the formula III

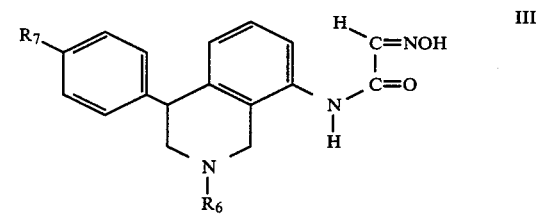

in which
R$_6$ and R$_7$ have the abovementioned meaning, are cyclized in the presence of a dehydrating agent.

Starting from the isatins of the formula Ia, other compounds of the formula I can be prepared. Thus, reduction of the isatins Ia with complex metal hydrides gives the indoles Ib

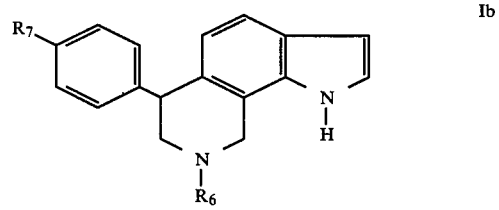

which can in turn be further reduced to the dihydroindoles Ic

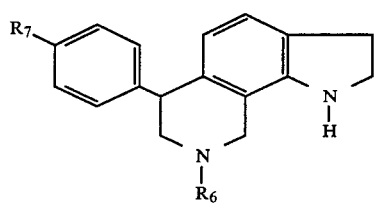
Ic

Reaction of the indoles Ib with Mannich reagents (n=1) or with oxalyl chloride (n=2) and then with a primary or secondary amine of the formula IV

IV in which $R_8$ and $R_9$ have the abovementioned meaning, with subsequent reduction leads to compounds of the formula Id with basic alkyl radicals in the indole ring.

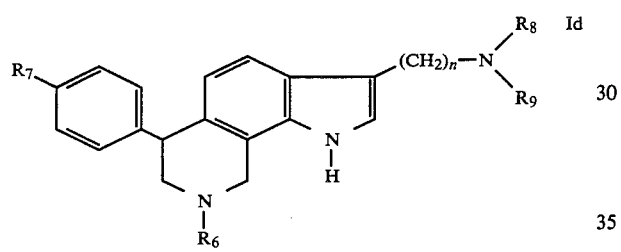
Id

Further reaction of the compounds of the formula Id (n=2) with formaldehyde gives β-carbolines of the formula Ie.

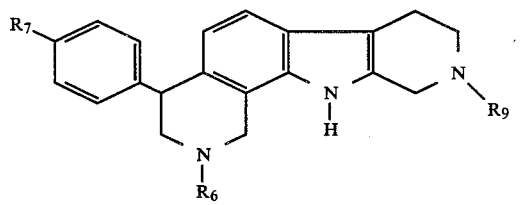
Ie

Compounds of the formula If are obtained from the isatins of the formula Ia when the keto function is ketalized with ethylene glycol, the acid amide function is sulphurized with Lawesson's reagent and the thioamide function is then converted into an amidine function with primary or secondary amines of the formula IV.

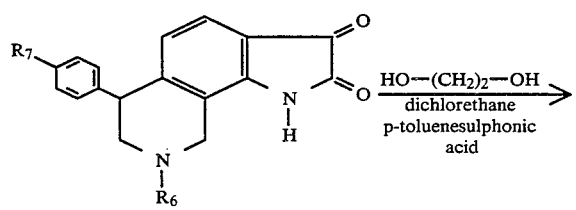

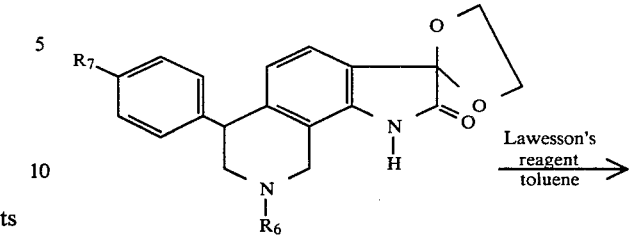

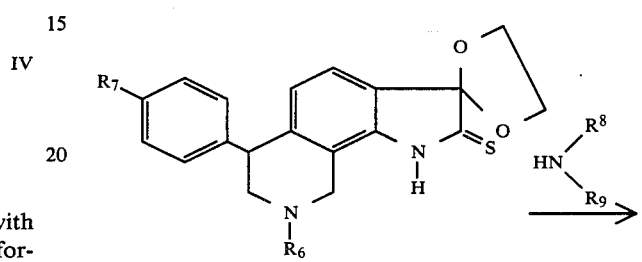

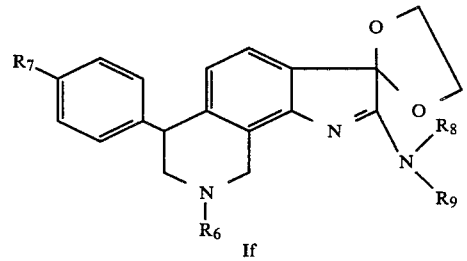
If

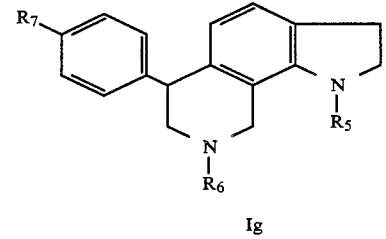
Ig are obtained from compounds of the formula Ic by reductive alkylation with $C_1$–$C_4$-aldehydes and $NaCNBH_3$.

Reaction of compounds of the formula Ic with acid amides of the formula V

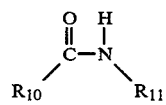
V in which $R_{10}$ and $R_{11}$ have the abovementioned meaning, and $POCl_3$ gives the compounds of the formula Ih.

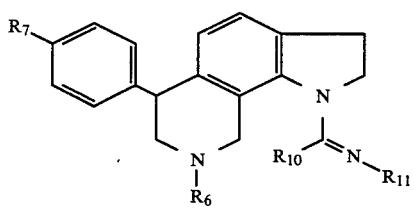

Ih

The active compounds of the general formula I according to the invention exhibit a marked effect on the central nervous system. They display anxiolytic and nootropic actions, and in particular also antidepressive actions. They are therefore particularly suitable for the treatment of depressive conditions and thus represent an enrichment of the range of medicaments.

Preferred compounds of the formula I are those in which $R_1$ represents H or $C_1$–$C_3$-alkyl, which is substituted by the radical

wherein
  $R_8$ and $R_9$ independently of one another represent H or $C_1$–$C_4$-alkyl or, together with the N atom, form a piperidine, pyrrolidine, morpholine or piperazine ring,
  $R_4$ represents H,
  $R_2$ and $R_3$ represent H or form a bond,
  $R_5$ represents H,
  $R_6$ represents $CH_3$ and
  $R_7$ represents H or F.

Particularly preferred compounds of the formula I are those
in which
  $R_1$ and $R_4$ represent H,
  $R_2$ and $R_3$ represent H or form a bond,
  $R_5$ represents H,
  $R_6$ represents $CH_3$ and
  $R_7$ represents F.

The preparation of compounds of the formula Ia is illustrated, by way of example, by the following equation:

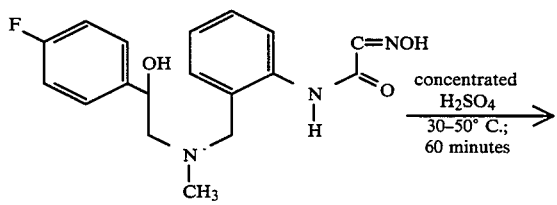

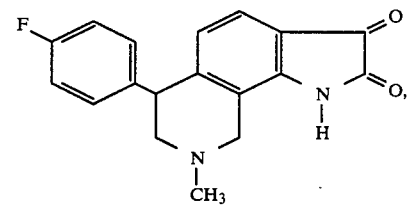

Another process for the preparation of compounds of the formula Ia is illustrated, by way of example, by the following equation:

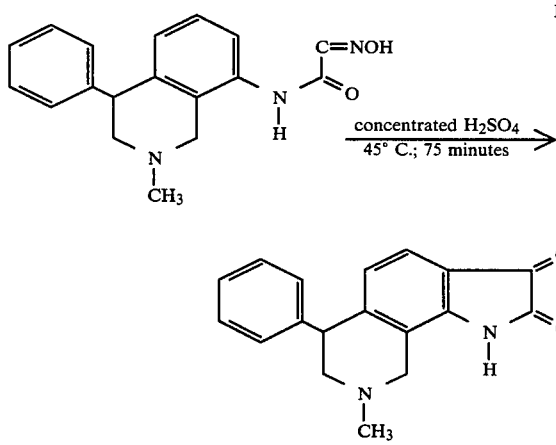

The two equations below illustrate, by way of example, the preparation of compounds of the formulae Ib and Ic:

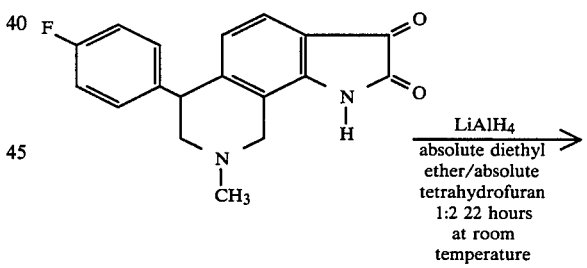

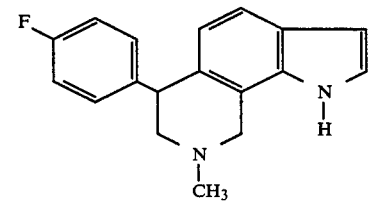

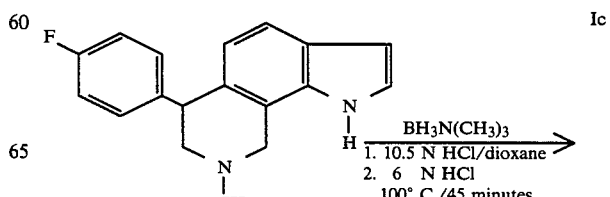

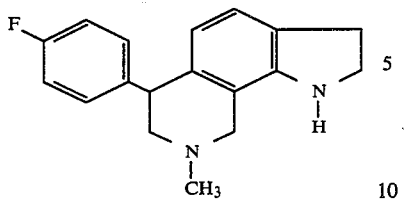
Starting from the compounds Ic, the compounds Ig and Ih are obtained as illustrated by way of example, by the following equations:
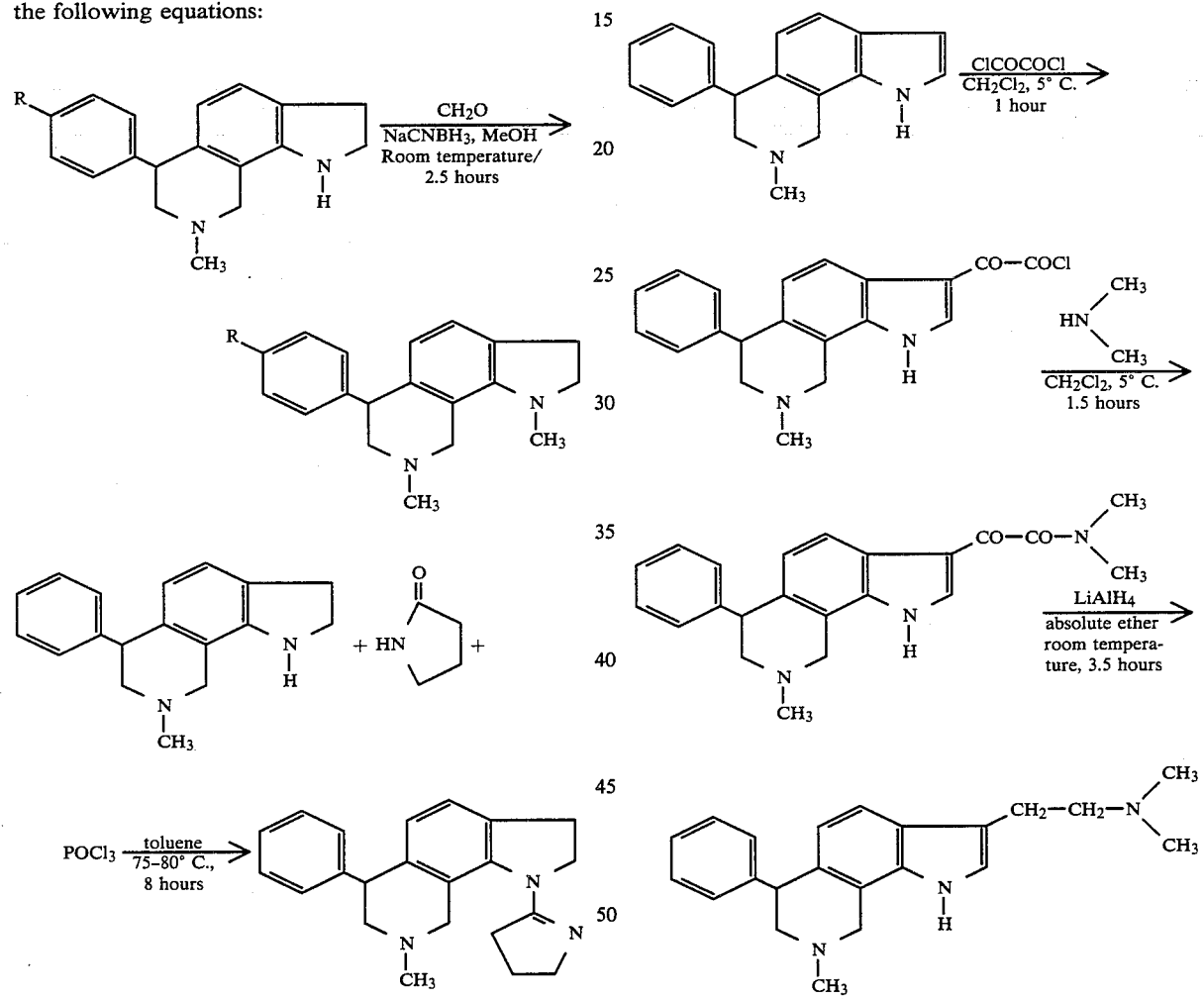
The two following examples illustrate the preparation of the compounds of the formula Id:
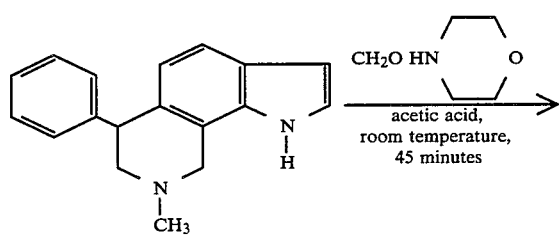
Carbolines of the formula Ie are obtained by the reaction route illustrated by the following example:
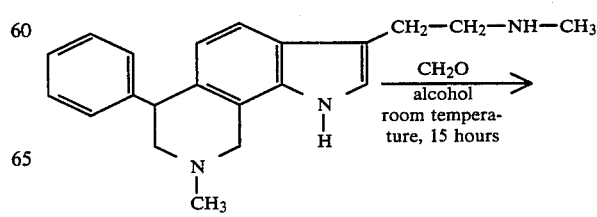

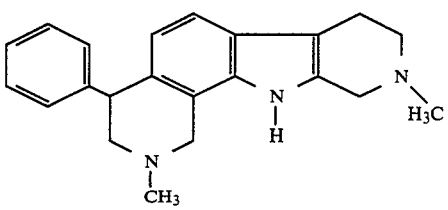

The following equation describes, by way of example, the preparation of amidines of the formula If:

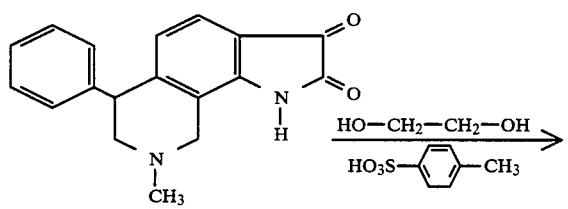

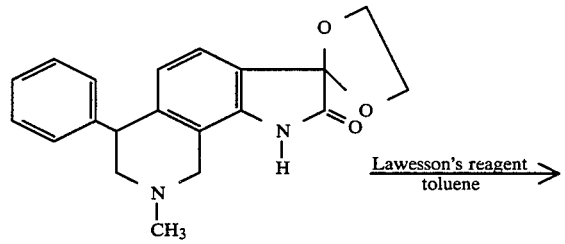

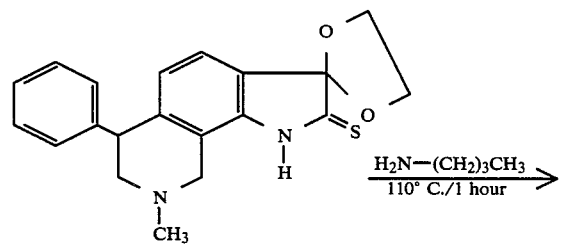

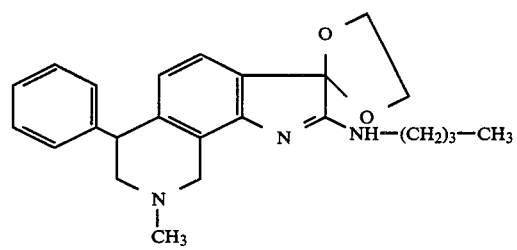

The reaction of the oximes II to give the isatins Ia is carried out in a strong dehydrating acid as the solvent. Suitable acids of this type are concentrated sulphuric acid or polyphosphoric acid. The reaction can be carried out at temperatures between about 10° C. and 120° C. The reaction is preferably carried out between 30° C. and 80° C., in particular between 40° C. and 50° C. The reaction times vary between a few minutes and some hours, depending on the temperature. If the reaction is carried out between 40° C. and 50° C., the reaction time is about 1 hour.

The reaction of the oximes III to give the isatins Ia is also carried out under the same reaction conditions.

The reduction of the isatins Ia to the indoles Ib is preferably carried out with complex metal hydrides, in particular with LiAlH$_4$. Solvents which are used are inert aprotic solvents, in particular ethers, such as diethyl ether, tetrahydrofuran, dioxane, 1,2-dimethoxyethane, diglyme or mixtures of these solvents. The reaction is carried out at temperatures between room temperature and the boiling point of the solvent, in particular at room temperature.

The reduction of the indoles Ib to the dihydroindoles Ic is preferably carried out with boron hydride compounds. Aminoborane complexes or NaBH$_4$ or NaCNBH$_3$ in organic acids, such as acetic acid or trifluoroacetic acid, are preferably used. The solvents used are mixtures of aqueous mineral acids, for example aqueous hydrochloric acid, with organic solvents, such as dioxane, tetrahydrofuran or ethanol, or organic carboxylic acids, such as acetic acid or trifluoroacetic acid. The reaction is carried out at temperatures between room temperature and the boiling point of the solvent. Mixtures of organic solvents with aqueous mineral acids or organic acids, or aqueous organic acids are used as the solvent for the preparation of the Mannich bases Id (n=1) from the indoles Ib. The reaction is preferably carried out in aqueous acetic acid. The reaction is carried out between 0° C. and 100° C., preferably at room temperature.

The indoles Ib are reacted with oxalyl chloride to prepare the compounds Id (n=2) in an inert organic solvent in the presence of an acid-binding agent.

Preferred solvents which may be mentioned are: dioxane, tetrahydrofuran, toluene, chlorobenzene, methylene chloride and dichloroethane. The acid-binding agents used are inorganic salts, such as potassium carbonate or sodium bicarbonate, or tertiary organic bases, such as triethylamine or diaminobutyric acid. The use of dioxane as the solvent and K$_2$CO$_3$ as the acid-binding agent is particularly preferred.

The reaction is carried out at temperatures between −20° C. and 60° C., preferably at about 0° C. Further reaction of the intermediates thus obtained with amines of the formula IV is carried out under the same reaction conditions as described above, preferably in dioxane as the solvent and with K$_2$CO$_3$ as the auxiliary base.

The reaction of these intermediates to compounds of the formula Id (n=2) is preferably carried out with complex metal hydrides, in particular with LiAlH$_4$. The solvents used are inert aprotic solvents, in particular ethers, such as diethyl ether, tetrahydrofuran, dioxane, 1,2-dimethoxyethane, diglyme or mixtures of these solvents. Absolute tetrahydrofuran is particularly preferably used as the solvent. The reaction is carried out at temperatures between room temperature and the boiling point of the solvent, particularly preferably at the boiling point of the solvent.

The reaction of compounds of the formula Id (n=2, R$_8$=H) with formaldehyde to give β-carbolines of the formula Ie is preferably carried out in aqueous mineral acids; the use of aqueous hydrochloric acid is particularly preferred. The reaction is carried out between 0° and 80° C., preferably at room temperature.

The reaction of the isatins Ia with ethylene glycol to prepare compounds If is carried out in an inert organic solvent by boiling in the presence of an acid catalyst, using a water separator. Solvents which may be mentioned are: dichloroethane, toluene and chlorobenzene. The use of dichloroethane as the solvent and p-toluenesulphonic acid as the catalyst is preferred.

The sulphurization of the intermediates thus obtained is carried out with Lawesson's reagent

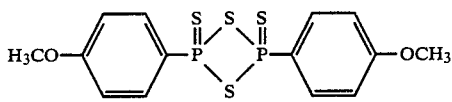

or $P_2S_5$ in an inert organic solvent. Toluene, xylene, dimethoxyethane, tetrahydrofuran or dioxane is used as such a solvent. The use of toluene as the solvent is particularly preferred. The reaction is preferably carried out at the boiling point of the solvent.

The reaction of the thioamides thus obtained with amines of the formula IV to give the amidines of the formula If can be carried out with or without a solvent. An excess of amine of the formula IV is preferably used as the solvent. The reaction is carried out at temperatures between 50° C. and 150° C., preferably at temperatures between 80° C. and 120° C.

Compounds of the formula Ig ($R_5 = C_1-C_4$-alkyl) are prepared by alkylation of the amines Ic. Reductive alkylation of the amines Ic with aldehydes and ketones in the presence of a hydrogen donor is preferred. Polar organic solvents or mixtures thereof with water are used as the solvent. The use of alcohols as the solvent, in particular the use of methanol, is preferred. The reaction is carried out in a pH range between 3 and 8, preferably in a pH range between 5 and 6. This pH value is preferably established by addition of an organic acid, in particular by addition of acetic acid. The reaction is carried out at temperatures between 0° C. and the boiling point of the solvent; the reaction is preferably carried out at room temperature.

Reaction of the amines Ic with acid amides of the formula V in the presence of $POCl_3$ to give amidines of the formula Ih is carried out in inert organic solvents. Toluene, xylene, dichloroethane, chloroform, tetrahydrofuran and dioxane may be mentioned. Toluene is preferably used. The reaction of the acid amide with $POCl_3$ is carried out at temperatures between 0° and 80° C. The reaction is preferably carried out at room temperature. The reaction of the amine with the activated acid amide is carried out at temperatures between room temperature and the boiling point of the solvent. The reaction is preferably carried out between 70° C. and 90° C.

The starting substances of the formula II are new. They can be prepared from the amines of the formula VI

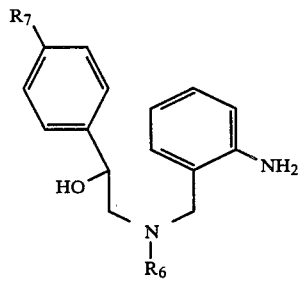

by reaction with chloral hydrate and hydroxylamine. (Sandmeyer isatin synthesis (Krauch, Kunz; Reaktionen der organischen Chemie (Reactions of Organic Chemistry), Dr. Alfred Hüthig, Verlag Heidelberg, 5th edition).)

Some of the amines are known. Where they are new, they can be prepared by processes which are known from the literature, such as those described in German Patent Application DE-PS No. 1,670,694.

The starting substances of the formula III are new. They can be prepared from amines of the formula VII

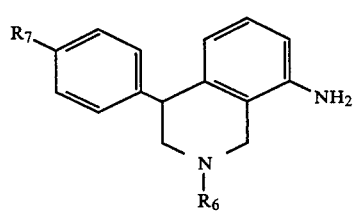

(Sandmeyer isatin synthesis).

Some of the amines of the formula VII are known from German Patent Application DE-PS No. 1,670,694. New compounds of the formula VII can be prepared analogously to the compounds described therein.

The present invention includes pharmaceutical formulations which, in addition to non-toxic, inert pharmaceutically suitable excipients, contain one or more compounds of the above general formula I, or which consist of one or more compounds of the above formula, as well as processes for the preparation of these formulations.

The present invention also includes pharmaceutical formulations in dosage units. This means that the formulations are in the form of individual parts, for example tablets, dragees, capsules, pills, suppositories and ampules of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions may be mentioned as preferred pharmaceutical formulations.

Tablets, dragrees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc stearate, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene-glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, micro-crystalline cellulose, aluminum methane hydroxide, bentonite, agar-agar and tragacanth, or mixtures of these substances.

The formulation forms mentioned can also contain colorants, preservatives and additives which improve the odor and flavor for example peppermint oil and eucalyptus oil, and sweeteners, for example saccharine.

The therapeutically active compounds should be present in the abovementioned pharmaceutical formulations in a concentration of about 0.1 to 99.5, preferably of about 0.5 to 95, % by weight of the total mixture.

The abovementioned pharmaceutial formulations can also contain other pharmaceutically active compounds in addition to active compounds of the above formula.

The abovementioned pharmaceutical formulations are prepared in the customary manner according to known methods, for example by mixing the active compound or compounds with the excipient or excipients.

The present invention also includes the use of the compounds of the above formula and the use of pharmaceutical formulations which contain one or more compounds of the abovementioned formula, in human and veterinary medicine, for the prevention, alleviation and/or cure of the abovementioned diseases.

The active compounds or the pharmaceutical formulations can be administered orally, parenterally, intraperitoneally and/or rectally, preferably orally, if appropriate in a formulation which is resistant to gastric juice.

In general, it has proved advantageous to administer the active compound or compounds orally in amounts of about 0.01 to about 100, preferably 0.1 to 10, mg/kg of body weight every 24 hours, distributed over 1 to 6 administrations, and in particular before and/or during and/or after meals. An individual dose contains the active compound or active compounds in amounts of, preferably, about 0.1 to about 5 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place. Thus it can in some cases suffice to manage with less than the abovementioned amount of active compound, but in other cases the abovementioned amount of active compound must be exceeded. The particular optimum dosage required and the type of administration of the active compounds can easily be determined by anyone skilled in the art on the basis of his expert knowledge.

Some test results for the new compounds of the general formula I which were tested for anxiolytic, nootropic and antidepressive properties are given below. The pilot tests used were inhibition of footshock induced aggression (Tedeschi et al., J. Pharmacol. Exp. Ther. 129, p. 28–34, 1954), for the anxiolytic action and the antitetrabenazine test (J. L. Howard et al., in: Antidepressants: Neurochemical, Behavioral and Clinical Perspectives, edited by S. J. Enna et al., Raven Press N.Y., pages 107–120, 1981) and amphetamine potentiation test (J. L. Howard et al., in: Antidepressants: Neurochemical, Behavioral and Clinical Perspectives, edited by S. J. Enna et al., Raven Press N.Y., pages 107–120, 1981) for the antidepressive action.

The following values were found, for example, for the antidepressive actions of the substances according to the invention:

(1) Tetrabenazine antagonism

Substances having an antidepressive action antagonize the ptosis in mice induced by tetrabenazine. The $ED_{50}$ value indicates the dose at which the ptosis induced by 20 mg/kg of tetrabenazine intraperitoneally is reduced to 50%. Examples which may be mentioned here are:

| Compound | $ED_{50}$ (mg/kg intraperitoneally) |
| --- | --- |
| 1 a (as the free base) | 1.0 |
| 1 b (as the free base) | 2.0 |
| 2 a (as the maleate salt) | 0.3 |
| 2 b (as the maleate salt) | 0.2 |
| 3 a (as the hydrochloride) | 0.1 |
| 3 b (as the hydrochloride) | 0.01 |
| 4 (as the hydrochloride) | 0.01 |
| 7 a (as the hydrochloride) | 0.1 |
| 7 b (as the hydrochloride) | 0.1 |
| 6 c (as the hydrochloride) | 2.0 |

(2) Amphetamine potentiation

Substances having an antidepressive action potentiate the amphetamine-induced stereotype behavior in rats.

The $ED_{50}$ value given is the dose at which the amphetamine-induced behavior is intensified by 50% following intravenous administration of 2 mg/kg of DL-amphetamine sulphate. Examples which may be mentioned here are:

| Compound | ED$_{50}$ (mg/kg intra-peritoneally) |
| --- | --- |
| 2 a (as the maleate salt) | 2.4 |
| 2 b (as the maleate salt) | 3.9 |
| 3 a (as the hydrochloride) | 1.2 |
| 3 b (as the hydrochloride) | 2.2 |

The present invention may be illustrated in more detail by the following examples.

EXAMPLE 1

8-Methyl-6-(4-fluorophenyl)-6,7,8,9-tetrahydro-1H-pyrido[4,3-g]indole-2,3-dione

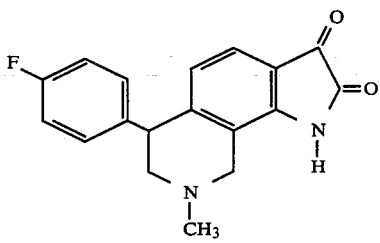

1a

A solution of 27 g (0.0781 mol) of 2-methyl-(2-(hydroxyiminoacetylamino)benzyl)amino-1-(4-fluorophenyl)-ethanol in 35 ml of CH$_2$Cl$_2$ is added dropwise, with stirring and in the absence of moisture, to 78 ml (1.37 mols) of concentrated H$_2$SO$_4$, which is warmed to 35° C., and the mixture is subsequently stirred at 45° C. for 1 hour. The reaction solution is poured onto 500 g of ice and brought to pH 6.8 at 0° C. with 25% strength NaOH. The precipitate is filtered off with suction, washed with H$_2$O and dried in a desiccator at 60° C. over P$_2$O$_5$ under a water pump vacuum.

Yield: 22.1 g (91%) of yellow-colored substance; melting point (micro-Kofler): 197°–200° C., with decomposition The following compound was prepared analogously:

8-Methyl-6-phenyl-6,7,8,9-tetrahydro-1H-pyrido[4,3-g]-indole-2,3-dione

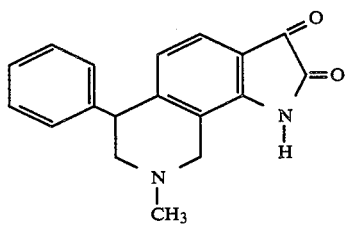

1b

Yield: 90% of theory; melting point (Mettler FP61): 214.7° C.

Preparation of the starting substances

2-Methyl(2-(hydroxyiminoacetylamino)benzyl)amino)-1-phenylethanol

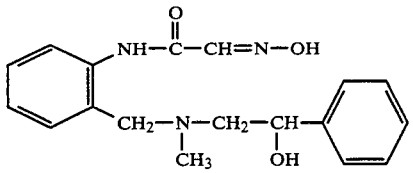

189.9 g (1.146 mols) of chloral hydrate are dissolved in 2.6 liters of H$_2$O, with stirring, and a solution of 306 g of 2-methyl(2-aminobenzyl)amino-1-phenylethanol in 666 ml of H$_2$O is added at room temperature. After 5 minutes, 1280 g of Na$_2$SO$_4$ and a solution of 229 g (3.297 mols) of hydroxylamine hydrochloride in 1.08 liters of H$_2$O are added. The mixture is then warmed to an internal temperature of 106° C. in the course of 40 minutes. The reaction temperature is kept at 106° C. for 2 minutes and is then brought to room temperature by rapid cooling with ice/H$_2$O. MeOH is added to the reaction mixture until the organic substances have dissolved. A pH value of 7.8 is established with 25% strength NaOH and the solvent is stripped off on a rotary evaporator. The aqueous phase is extracted with ethyl acetate, the organic phase is dried over Na$_2$SO$_4$ and the solvent is evaporated off on a rotary evaporator. The residue is freed from traces of solvent under an oil pump vacuum and is then dried in a desiccator over P$_2$O$_5$.

Yield: 317 g (91%)

The following compound was obtained by an analogous route:

2-(Methyl-(2-hydroxyiminoacetylamino)benzyl-)amino)-1-(4-fluorophenyl)ethanol

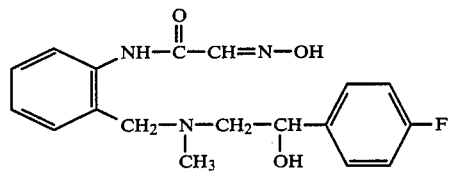

The crude product was chromatographed on silica gel 60 using ethyl acetate as the eluent.

Yield: 76% of theory.

2-(Methyl-(2-aminobenzyl)amino)-1-(4-fluorophenyl)ethanol

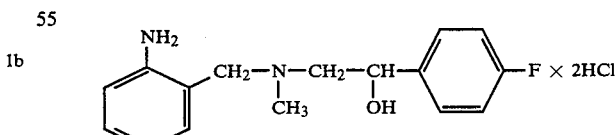

A solution of 124.5 g (0.409 mol) of 2-methyl-(2-nitrobenzyl)-amino-1-(4-fluorophenyl)ethanol in 150 ml of ethanol and 500 ml of ethyl acetate is hydrogenated with 1 g of PtO$_2$ at room temperature under atmospheric pressure until 3 molar equivalents of H$_2$ have been taken up. The catalyst is filtered off, the filtrate is evaporated on a rotary evaporator and the residue is dissolved in 450 ml of $CH_2Cl_2$. The $CH_2Cl_2$ phase is washed 3 times with 200 ml of $H_2O$ each time and dried over $Na_2SO_4$. After filtration, HCl/diethyl ether is added. The salt which has precipitated is filtered off with suction, washed with diethyl ether and dried in a desiccator over NaOH at 60° C. under a water pump vacuum.

Yield: 136 g of hygroscopic hydrochloride; melting point (micro-Kofler): 125°–127° C.

2-(Methyl(2-nitrobenzyl)amino-1-(4-fluorophenyl)ethanol

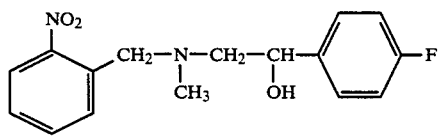

140 g (0.413 mol) of 2-(methyl-(2-nitrobenzyl)-amino)-1-(4-fluorophenyl)ethanone are dissolved in 82.8 ml of MeOH, the solution is cooled to 4° C. and a solution of 37.83 g (0.657 mol) of sodium borohydride in 270 ml of 0.1N NaOH is added dropwise in the course of 2 hours, with stirring. The reaction mixture is stirred at room temperature for 1 hour. It is concentrated on a rotary evaporator and the residue is extracted with ethyl acetate. The organic phase is dried over $Na_2SO_4$ and the solvent is stripped off. The oily residue is freed from traces of solvent under an oil pump vacuum.

Yield: 124.5 g (99%).

2-(Methyl-(2-nitrobenzyl)amino)-1-(4-fluorophenyl)ethanone

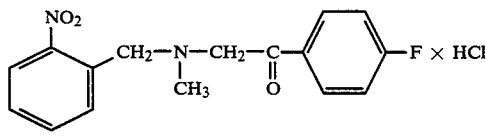

135.8 g (0.67 mol) of methyl-(2-nitrobenzyl)-amine and 187.5 ml (1.339 mols) of triethylamine are dissolved in 1.87 liters of ethanol at room temperature, with stirring, and 148 g (0.682 mol) of 2-bromo-1-(4-fluorophenyl)ethanone are then added in portions. The reaction mixture is stirred for 3 hours. The solvent is then stripped off on a rotary evaporator and the residue is dissolved in 1.3 liters of toluene. The toluene phase is washed several times with $H_2O$ and dried over $Na_2SO_4$, and HCl/diethyl ether is added. The glutinous precipitate is separated from the toluene by decanting and crystallized with acetone. The colorless precipitate is filtered off with suction and dried.

Yield: 158.5 g (70%); melting point (Mettler FP61): 171.9° C.

8-Methyl-6-phenyl-6,7,8,9-tetrahydro-1H-pyrido[4,3-g]-indole-2,3-dione

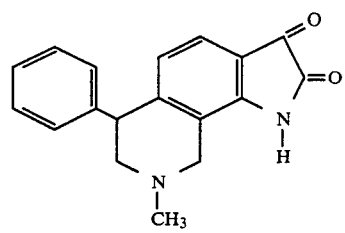

17.5 g (0.0566 mol) of N-methyl-4-phenyl-8-(hydroxyiminoacetylamino)isoquinoline were added in small portions to 43.75 ml of concentrated $H_2SO_4$ at 45° C. and the mixture was warmed at 45° C. for 75 minutes. It was cooled to room temperature and poured onto 450 g of ice. A pH of 6.8 was then established with 2N NaOH. The precipitate which had separated out was filtered off with suction and washed with water. After drying, 15.3 g (92.5% of theory) of orange-colored crude product are obtained. (Melting point of the pure product=about 188° C., decomposition).

Preparation of the starting compound:

N-Methyl-4-phenyl-8-(hydroxyiminoacetylamino)isoquinoline

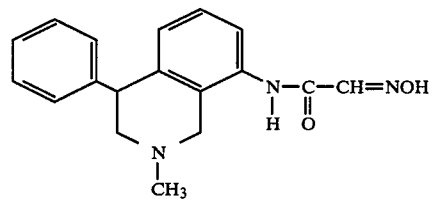

A solution of 10.75 g (0.0345 mol) of N-methyl-4-phenyl-8-amino-isoquinoline hydrochloride in 22 ml of $H_2O$ was added to 6.23 g (0.0376 mol) of chloral hydrate in 86 ml of water. After 5 minutes, 42.5 g of $Na_2SO_4$ and a solution of 7.6 g (0.109 mol) of hydroxylamine hydrochloride in 36 ml of $H_2O$ were added. The reaction mixture was warmed to 106° C. (internal temperature) in the course of 40 minutes. After 2 minutes, the mixture was cooled rapidly to 18° C. with ice/$H_2O$. 200 ml of methanol were added to the reaction mixture and a pH of 7.6 was established with 2N NaOH. The precipitate which had separated out was filtered off with suction and washed thoroughly with $H_2O$. After drying, 9.7 g (90.2% of theory) of crude product of melting point 151.3° C. (Mettler FP 61) were obtained.

EXAMPLE 2

8-Methyl-6-phenyl-6,7,8,9-tetrahydro-1H-pyrido[4,3-g]-indole

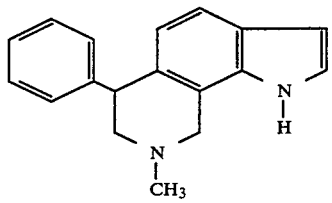

2a 20 g (0.524 mol) of LiAlH₄ are suspended in 400 ml of absolute diethyl ether at room temperature, with stirring, while flushing with nitrogen and in the absence of moisture. 550 ml of absolute tetrahydrofuran are then added, followed by 34 g (0.116 mol) of 8-methyl-6-phenyl-6,7,8,9-tetrahydro-1H-pyrido[4,3-g]indole-2,3-dione in portions. The reaction mixture is subsequently stirred at room temperature for 3½ hours. To dissociate the reaction complex, a solution of 42 ml of H₂O in 160 ml of tetrahydrofuran is added dropwise, with cooling. The inorganic solid is filtered off and the filtrate is freed from the solvent on a rotary evaporator. The residue is chromatographed on silica gel 60 with an eluent mixture of: ethyl acetate and 8.3% of MeOH. The pure substance is dried in a desiccator over P₂O₅ at 60° C. under a water pump vacuum.

Yield: 9.1 g (30%); melting point (Mettler FP61): 157.9° C.

The following compound was prepared analogously:

8-Methyl-6-(4-fluorophenyl)-6,7,8,9-tetrahydro-1H-pyrido-[4,3-g]indole

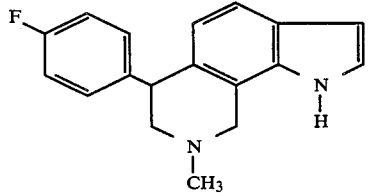

2b

Yield: 44% of theory; melting point (Mettler FP 61): 205.5° C.

Preparation of a salt with maleic acid 2.0 g (0.00713 mol) of 8-methyl-6-(4-fluorophenyl)-6,7,8,9-tetrahydro-1H-pyrido[4,3-g]indole are suspended in 10 ml of ethanol, and a solution of 0.91 g (0.00784 mol) of maleic acid in 10 ml of ethanol is added, with stirring. The reaction mixture is kept at room temperature for 1 hour. The crystalline product is filtered off with suction, washed with ethanol/ether and dried in a desiccator at 95° C. over P₂O₅ under a water pump vacuum.

Yield. 2.4 g (85%); melting point (Mettler FP 61): 170.5° C.

EXAMPLE 3

8-Methyl-6-phenyl-2,3,6,7,8,9-hexahydro-1H-pyrido[4,3-g]-indole

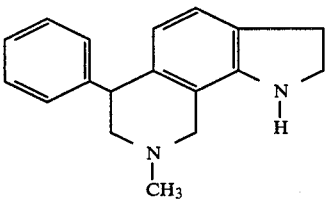

3a 12.5 ml (0.131 mol) of 10.5N hydrochloric acid are added dropwise to a mixture of 26 g (0.1 mol) of 8-methyl-6-phenyl-6,7,8,9-tetrahydro-1H-pyrido[4,3-g]indole and 29.2 g (0.4 mol) of trimethylaminoborane in 150 ml of absolute dioxane at a temperature of 16° C., with stirring and in the absence of moisture. The mixture is then heated under reflux for 30 minutes and cooled to room temperature, 50 ml (0.3 mol) of 6N HCl are added and the mixture is heated under reflux once more for 15 minutes. After cooling to room temperature, 600 ml of H₂O are added to the reaction mixture, the mixture is filtered over kieselguhr and, after addition of a further 600 ml of H₂O, the filtrate is brought to pH 9 with 20% strength NaOH. The aqueous phase is now extracted several times with CH₂Cl₂ and, after drying over Na₂SO₄, the solvent is distilled off on a rotary evaporator. The oily residue is chromatographed on silica gel (silica gel 60 from E. Merck, Darmstadt) using ethyl acetate and MeOH (20:7) as the eluent.

Yield: 29.5 g (62.5%); melting point (Mettler FP 61): 125.1° C.

The following compound was prepared analogously to Example 3:

8-Methyl-6-(4-fluorophenyl)-2,3,6,7,8,9-hexahydro-1H-pyrido[4,3-g]indole

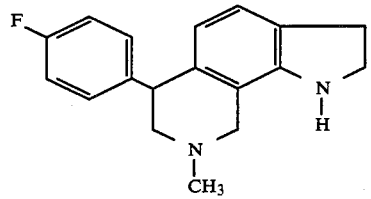

The crude product was chromatographed on silica gel (silica gel 60 from E. Merck, Darmstadt) using an eluent mixture of ethyl acetate and MeOH (2:1).

Yield: 3.0 g (43%); melting point (Mettler FP 61): 137.6° C.

Preparation of the hydrochloride

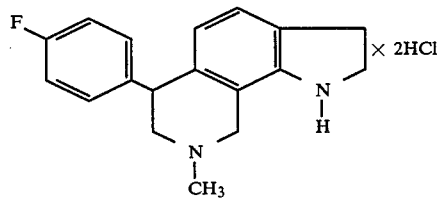

3b

The base is converted into the hydrochloride with ethereal hydrochloric acid.

Melting point (Mettler FP 61): 176.8° C.

EXAMPLE 4

1,8-Dimethyl-6-(fluorophenyl)-2,3,6,7,8,9-hexahydro-1H-pyrido[4,3-g]indole

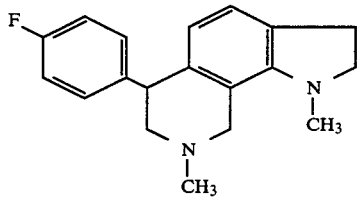

2.3 g (0.00814 mol) of 8-methyl-6-(fluorophenyl)-2,3,6,7,8,9-hexahydro-1H-pyrido[4,3-g]indole are dissolved in 20 ml of MeOH, and 0.977 g (0.0163 mol) of acetic acid and 0.791 ml (0.00976 mol) of formalin are added at room temperature, with stirring. The reaction mixture is subsequently stirred for 1 hour and 1.53 g (0.0244 mol) of sodium cyanoborohydride are then added in several portions. In order to bring the reaction to completion, the mixture is subsequently stirred at room temperature for 1.5 hours. The solvent is then stripped off on a rotary evaporator, $H_2O$ is added to the residue and the mixture is rendered alkaline with 1N NaOH. The aqueous phase is extracted with $CH_2Cl_2$ and dried over $NaSO_4$ and the solvent is evaporated off on a rotary evaporator. The oily residue is chromatographed on silica gel (silica gel 60 from E. Merck, Darmstadt) using an eluent mixture of: $CH_2Cl_2$/MeOH (2.5:0.15). The product is dried in the absence of light in a desiccator over $P_2O_5$ at $10^{-2}$ bar.

Yield: 1.8 g of a syrupy product.

Preparation of the hydrochloride

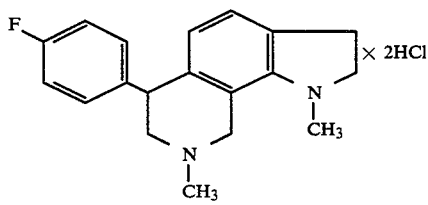

The base is converted into the hydrochloride with ethereal hydrochloric acid.

Melting point (Mettler FP 61): 188.8° C. (with decomposition)

EXAMPLE 5

1-(2-Pyrrolin-1-yl)-8-methyl-6-phenyl-2,3,6,7,8,9-hexahydro-1H-pyrido[4,3-g]indole

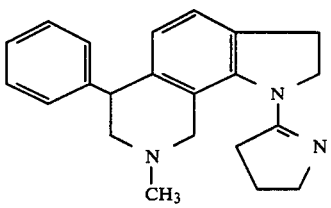

A solution of 1.9 ml (0.02 mol) of phosphorus oxychloride in 6 ml of toluene is added dropwise to a solution of 3.4 g (0.04 mol) of pyrrolid-2-one in 8 ml of toluene at a temperature between 2° and 0° C., with stirring and cooling. The mixture is stirred at room temperature for 1½ hours and left to stand overnight. A solution of 5.2 g (0.02 mol) of 8-methyl-6-phenyl-2,3,6,7,8,9-hexahydro-1H-pyrido[4,3-g]indole in 10 ml of toluene and 20 ml of $CH_2Cl_2$ is then added. The $CH_2Cl_2$ is distilled off and the reaction mixture is stirred at a temperature between 75° and 80° C. for 8 hours, with stirring. The solid which has precipitated is filtered off with suction, and 2N NaOH and $H_2O$ are added in order to convert it into the free base. The aqueous phase is extracted with $CH_2Cl_2$, the $CH_2Cl_2$ phase is dried and the solvent is removed. The residue is chromatographed on silica gel 60 from E. Merck, Darmstadt) using an eluent mixture of $CH_2Cl_2$/MeOH (2:1), and on aluminum oxide (aluminum oxide 90 from E. Merck, Darmstadt) using an eluent mixture of $CH_2Cl_2$ and MeOH (20:0.25). The product is dried in a desiccator over $P_2O_5$ under a water pump vacuum.

Yield: 3.5 g (52.8%); melting point (Mettler FP 61): 57.9° C.

EXAMPLE 6

3-(1-Piperidinylmethyl)-6-phenyl-8-methyl-2,3,6,7,8,9-hexahydro-1H-pyrido[4,3-g]indole

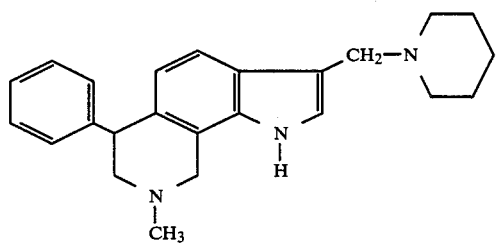

An ice-cooled solution of 1.51 ml (0.01524 mol) of piperidine and 1.14 ml of $H_2O$ in 4.6 ml of acetic acid is added, together with 1.14 ml (0.014 mol) of formalin, all at once, to 2.0 g (0.00762 mol) of 8-methyl-6-phenyl-6,7,8,9-tetrahydro-1H-pyrido[4,3-g]indole, with stirring and while flushing with nitrogen. The mixture is then rendered alkaline with 2N NaOH and extracted with $CH_2Cl_2$. The $CH_2Cl_2$ phase is dried over $Na_2SO_4$ and the solvent is stripped off on a rotary evaporator. The residue is chromatographed on silica gel (silica gel 60 from e. Merck, Darmstadt) using an eluent mixture of $CH_2Cl_2$/MeOH/$N(C_2H_5)_3$ (15:6:0.5). The product is dried in a desiccator over $P_2O_5$ under a water pump vacuum.

Yield: 3.1 g (89.6%); melting point (Mettler FP 61): 80.4° C.

Preparation of the hydrochloride

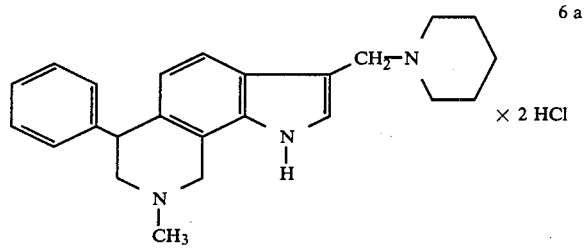

The base is converted into the hydrochloride in MeOH with 1N aqueous HCl. After the solvent has been removed, the product is dried in a desiccator over NaOH under a water pump vacuum at 95° C.

Yield: 3.3 g (91.5%); melting point (Mettler FP 61): 212.8° C.

The following compounds were prepared analogously to Example 6:

3-Dimethylaminomethyl-8-methyl-6-phenyl-6,7,8,9-tetrahydro-1H-pyrido[4,3-g]indole

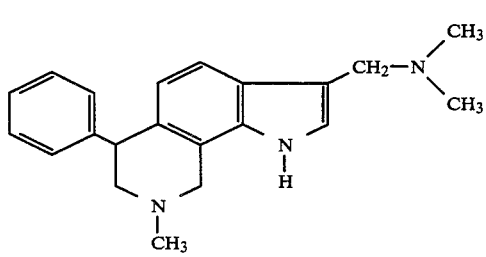

Yield: 78% of theory; melting point (Mettler FP 61): 80.9° C.

Preparation of the hydrochloride

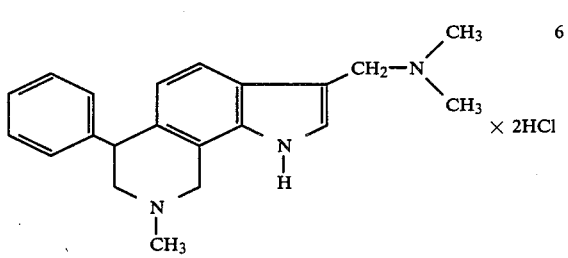

The hydrochloride was obtained in MeOH with 1N aqueous HCl. Melting point (Mettler FP 61): 203° C.

3-(4-Morpholinylmethyl)-8-methyl-6-phenyl-6,7,8,9-tetrahydro-1H-pyrido[4,3-g]indole

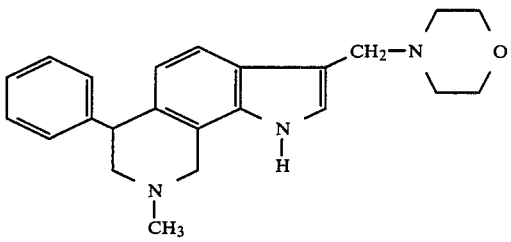

The crude product was chromatographed on silica gel (silica gel 60 from E. Merck, Darmstadt) using an eluent mixture of $CH_2Cl_2/MeOH/N(C_2H_5)_3$ (15:6:0.5), and the substance was dried in a desiccator.

Yield: 97.5% of theory; melting point (Mettler FP 61): 77.3° C.

Preparation of the hydrochloride

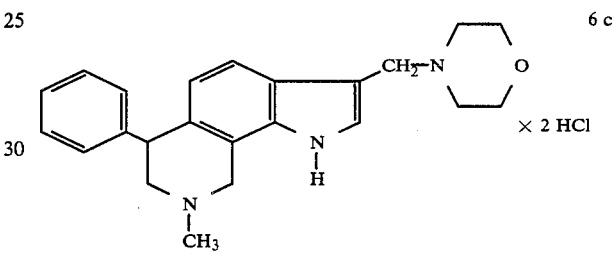

The hydrochloride was prepared in MeOH with 1N aqueous HCl. Melting point (Mettler FP 61): 257° C.

EXAMPLE 7

3-Methylaminoethyl-8-methyl-6phenyl-6,7,8,9-tetrahydro-1H-pyrido[4,3-g]indole

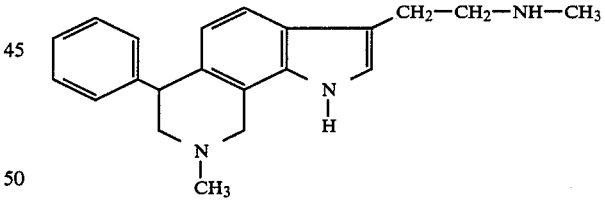

4.9 g (0.129 mol) of $LiAlH_4$ are initially introduced into 69.5 ml of absolute tetrahydrofuran, nitrogen is passed over and a solution of 11.3 g (0.0325 mol) of 3-(8-methyl-6-phenyl-6,7,8,9-tetrahydro-1H-pyrido[4,3-g]-indolyl)-2-oxo-acetic acid methylamide in 50 ml of absolute tetrahydrofuran is added dropwise in the course of 15 minutes at room temperature, with stirring and in the absence of moisture. The mixture is then heated at the reflux temperature for 12 hours. A solution of 10 ml of $H_2O$ in 40 ml of tetrahydrofuran is then added dropwise to the reaction mixture, with cooling and stirring. The inorganic content is filtered off with suction and the residue on the filter is washed thoroughly with $CH_2Cl_2$. The filtrate is then concentrated on a rotary evaporator and the residue is chromatographed on silica gel (silica gel 60 from E. Merck, Darmstadt) over a column with an eluent mixture of CH₂Cl₂/MeOH/N(C₂H₅)₃ (15:10:0.5).

Yield: 3.9 g (37%).

Preparation of the hydrochloride

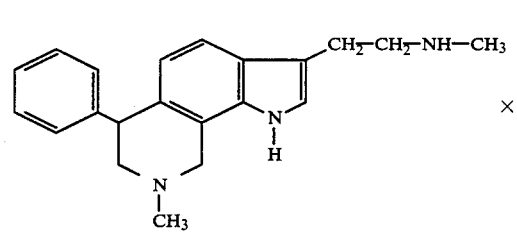

× 2 HCl 7 a

To prepare the hydrochloride, the base is dissolved in CH₂Cl₂ and ethereal hydrochloric acid is added to the solution. The solvent is stripped off and the residue is triturated with ether. The HCl salt is dried over NaOH at 70° C. under a water pump vacuum.

Melting point (Mettler FP 61): 167.4° C.

The following compound was prepared analogously:

3-(Isopropylaminoethyl)-8-methyl-6-phenyl-6,7,8,9-tetrahydro-1H-pyrido[4,3-g]indole

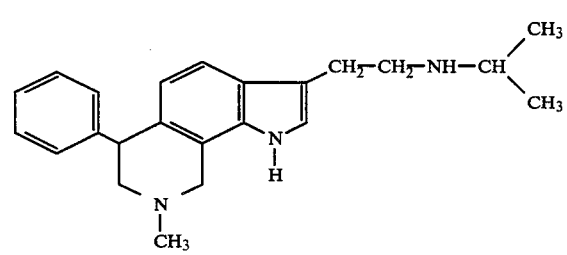

The crude product was chromatographed on silica gel (silica gel 60 from E. Merck, Darmstadt) using an eluent mixture of: CH₂Cl₂/MeOH/N(C₂H₅)₃ (15:6:0.5). The substance was then dried in a desiccator over P₂O₅ under a water pump vacuum.

Yield: 65% of theory.

Preparation of the hydrochloride

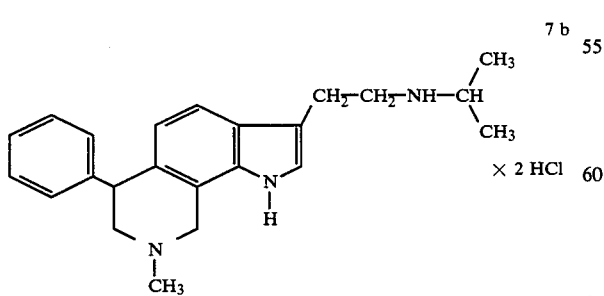

× 2 HCl 7 b

The hydrochloride was obtained as described above.
Melting point (Mettler FP 61): 223.5° C.

Preparation of the starting compounds 3-(8-Methyl-6-phenyl-6,7,8,9-tetrahydro-1H-pyrido[4,3-g]-indol-yl)-2-oxo-acetic acid methylamide

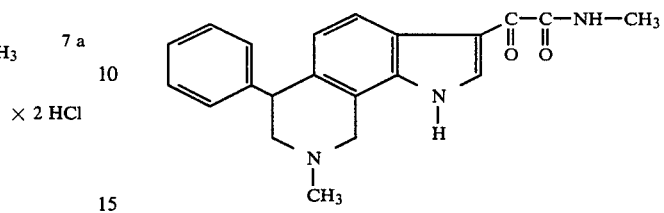

7.92 ml (0.0918 mol) of oxalyl chloride are added to 5.5 g (0.0397 mol) of K₂CO₃ in 78.5 ml of absolute dioxane and the mixture is cooled to 0° C. in the absence of moisture. A solution of 8-methyl-6-phenyl-6,7,8,9-tetrahydro-1H-pyrido[4,3-g]indole in 196 ml of absolute dioxane is now added dropwise in the course of 30 minutes, with stirring, and the mixture is subsequently stirred at room temperature for 16 hours in order to bring the reaction to completion. 10.9 g (0.0791 mol) of K₂co₃ are then added, a solution of 12.1 g (0.389 mol) of anhydrous methylamine in 100 ml of absolute dioxane is subsequently added dropwise and the mixture is allowed to after-react for 2½ hours. The solvent is stripped off on a rotary evaporator; 150 ml of H₂O are added to the residue and the aqueous phase is extracted by shaking with 150 ml of diethyl ether. The insoluble substance content is filtered off, washed with 50 ml of CH₂Cl₂ and dried over P₂O₅ at 60° C. under a water pump vacuum.

Yield: 10.1 g (74%); melting point (Mettler FP 61): 224.7° C.

The following compound was obtained by an analogous route:

3-(8-Methyl-6-phenyl-6,7,8,9-tetrahydro-1H-pyrido[4,3-g]-indol-yl)-2-oxo-acetic acid isopropylamide

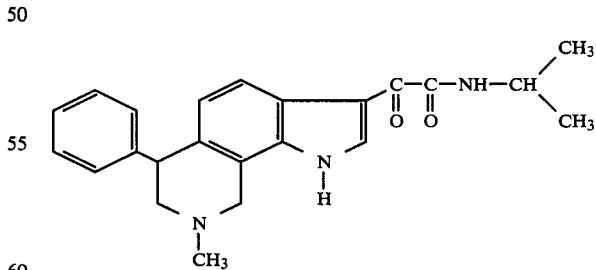

The crude product was chromatographed on silica gel (silica gel 60 from E. Merck, Darmstadt) using an eluent mixture of ethyl acetate and MeOH (9:1). The substance was then dried over P₂O₅ under a water pump vacuum.

Yield: 65% of theory.

Preparation of the hydrochloride

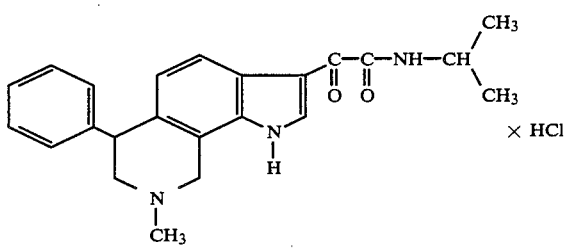

The hydrochloride was prepared as described for the salts of Example 7.
Melting point (Mettler FP 61): 257.6° C.

EXAMPLE 8

3-(Isopropylaminoethyl)-8-methyl-6-phenyl-2,3,6,7,8,9-hexahydro-1H-pyrido[4,3-g]indole

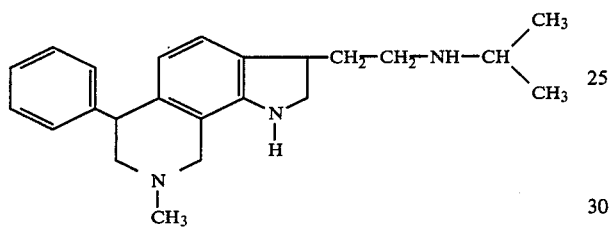

2.1 g (0.00604 mol) of 3-(isopropylaminoethyl)-8-methyl-6-phenyl-6,7,8,9-tetrahydro-1H-pyrido[4,3-g]-indole are dissolved in 25 ml (0.3275 mol) of trifluoroacetic acid, with stirring and in the absence of moisture, and a solution of 1.76 g (0.0241 mol) of trimethylaminoborane in 10 ml of tetrahydrofuran is then added dropwise at a temperature of 0°−+2° C. The mixture is subsequently stirred at 0° C. for 1 hour, a solution of 1.76 g (0.0241 mol) of trimethylamonoborane in 10 ml of tetrahydrofuran is then again added and the mixture is subsequently stirred for 2.5 hours. 150 ml of H$_2$O are now added to the reaction mixture, the mixture is brought to pH 13 with NaOH and the oily product which deposits is extracted with CH$_2$Cl$_2$. The CH$_2$Cl$_2$ phase is washed with H$_2$O, dried over Na$_2$SO$_4$ and then freed from the solvent on a rotary evaporator. The residue is chromatographed twice on silica gel (silica gel 60 from E. Merck, Darmstadt). Eluent: initially CH$_2$Cl$_2$/MeOH/N(C$_2$H$_5$)$_3$ (15:4:0.25), then diethyl ether/MeOH/N(C$_2$H$_5$)$_3$ (15:3:0.25).

Yield: 1.3 g of a colorless syrupy substance (61.5%).

Preparation of the hydrochloride

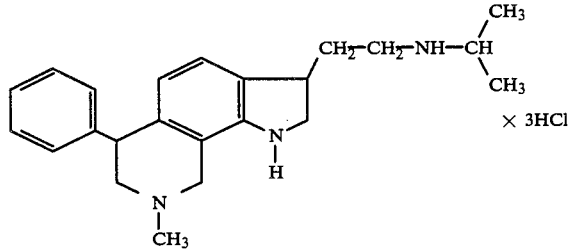

The hydrochloride was obtained as described in Example 7.

Melting point (Mettler FP 61): 223° C.

EXAMPLE 9

3,7-Dimethyl-9-phenyl-1,2,3,4,6,7,8,9-octahydro-5H-dipyrido[4,3-g:3',4'-b]indole

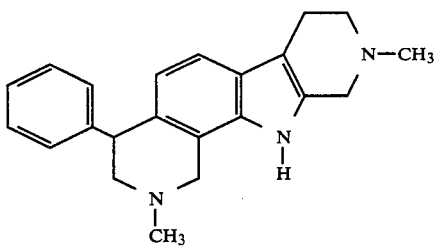

0.15 ml of 1N HCl (0.00015 mol) is added to 0.8 g (0.0025 mol) of 3-(methylaminoethyl)-8-methyl-6-phenyl-6,7,8,9-tetrahydro-1H-pyrido[4,3-g]indole, 0.23 ml (0.0028 mol) of 40% strength formalin solution and 1.5 ml of 0.1N HCl (0.00015 mol) and the mixture is then stirred at room temperature for 2 hours. The crystalline substance which forms is dissolved with 2 ml of ethyl alcohol and the solution is left to stand overnight. The solvent is stripped off on a rotary evaporator, aqueous KHCO$_3$ solution is added to the residue and the aqueous phase is extracted with CH$_2$Cl$_2$. The CH$_2$Cl phase is dried over Na$_2$SO$_4$ and the solvent is stripped off on a rotary evaporator. The residue is separated on silica gel (silica gel 60 from E. Merck, Darmstadt) over a column with the eluent ethyl acetate/MeOH/(N(C$_2$H$_5$)$_3$ (9:3.5:0.25).

Yield: 0.6 g (73%).

Preparation of the hydrochloride

The hydrochloride of the base was obtained analogously to Example 7.

Melting point (micro-Kofler): 236°–237° C.

EXAMPLE 10

2-(N-Piperidino)-3-ethylenedioxy-6-phenyl-8-methyl-6,7,8,9-tetrahydro-3H-pyrido[4,3-g]indole

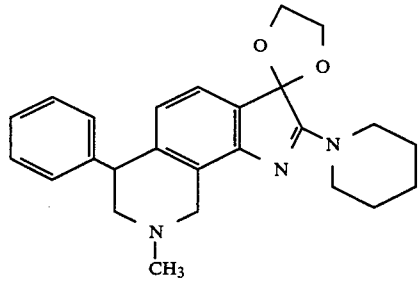

10 a 3,1 g (0.00879 mol) of 2-thiono-3-ethylenedioxy-6-phenyl-8-methyl-2,3,6,7,8,9-hexahydro-1H-pyrido[4,3-g]-indole are dissolved in 42.5 ml (0.429 mol) of piperidine, with stirring, and the mixture is warmed at 110° C. for 1 hour, in the absence of moisture and while flushing with nitrogen. The excess piperidine is distilled off on a rotary evaporator, the residue is dissolved in CH$_2$Cl$_2$ and the CH$_2$Cl$_2$ phase is extracted 3 times with H$_2$O. The organic phase is dried over Na$_2$SO$_4$ and the solvent is stripped off on a rotary evaporator. The residue is chromatographed on aluminum oxide (aluminum oxide 90 from E. Merck, Darmstadt) using an eluent mixture of methylene chloride/methanol (20;0.05). The substance is dried over P$_2$O$_5$ under a water pump vacuum.

Yield: 1.1 g (24.5%); melting point (micro-Kofler): 215°–216° C.

The following compound was obtained analogously to Example 10:

2-Butylimino-3-ethylenedioxy-6-phenyl-8-methyl-2,3,6,7,8,9-hexahydro-1H-pyrido[4,3-g]indole

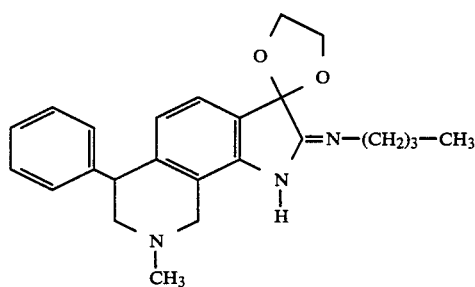

10 b

The crude product was chromatographed on silica gel (silica gel 60 from E. Merck, Darmstadt) using an eluent mixture of ethyl acetate and methanol (9:1). The pure substance was dried over P$_2$O$_5$ at 60° C. under a water pump vacuum.

Yield: 49% of theory; melting point (Mettler FP 61): 87.3° C.

Preparation of the starting substances

2-Thiono-3-ethylenedioxy-6-phenyl-8-methyl-2,3,6,7,8,9-hexahydro-1H-pyrido-[4,3-g]indole

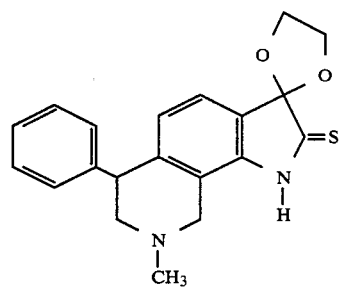

A suspension of 1.68 g (0.005 mol) of 2-oxo-3-ethylenedioxy-6-phenyl-8-methyl-2,3,6,7,8,9-hexahydro-1H-pyrido[4,3-g]indole and 1.0 g (0.0025 mol) of Lawessson's reagent in 10 ml of absolute toluene is heated at the reflux temperature for 1 hour, in the absence of moisture and with stirring. The reaction mixture is then freed from the solvent on a rotary evaporator and the residue is chromatographed on silica gel (silica gel 60 from E. Merck, Darmstadt) using an eluent mixture of CH$_2$Cl$_2$ and MeOH (20:1). The substance is dried over P$_2$O$_5$ under a water pump vacuum.

Yield: 0.85 g (49%).

2-Oxo-3-ethylenedioxy-6-phenyl-8-methyl-2,3,6,7,8,9-hexahydro-1H-pyrido[4,3-g]indole

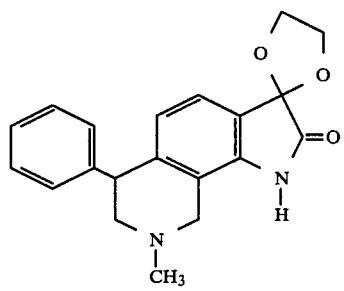

100 ml of dichloroethane are added to 20.6 g (0.0624 mol) of 8-methyl-6-phenyl-6,7,8,9-tetrahydro-1H-pyrido[4,3-g]indole-2,3-dione, 21 ml (0.374 mol) of ethylene glycol and 0.336 g (0.00176 mol) of toluene-4-sulphonic acid monohydrate, with stirring, and the mixture is heated under reflux for 3.5 hours, using a water separator. Ice is added to the reaction mixture and the mixture is brought to pH 6.8 with aqueous KHCO$_3$ solution. The mixture is extracted with CH$_2$Cl$_2$, the CH$_2$Cl$_2$ phase is washed with H$_2$O and dried over Na$_2$SO$_4$ and the solvent is stripped off in a rotary evaporator. The residue is chromatographed on Al$_2$O$_3$ (aluminum oxide from E. Merck, Darmstadt) using an eluent mixture of ethyl acetate and MeOH (20:0.2). After trituration with ethyl acetate/petroleum ether, the substance becomes crystalline. It is dried over P$_2$O$_5$ at 80° C. in vacuo.

Yield: 12.5 g (59.5%);
melting point (Mettler FP 61): 221.2° C.

It is understood that the specification and examples are illustrative but not limitative of the present inven-

We claim:

1. A pyridoindole of the formula

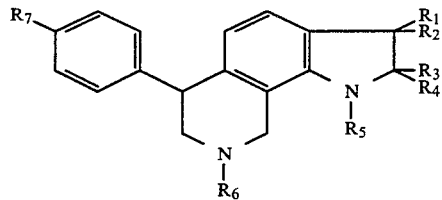

in which
R$_1$ represents hydrogen or C$_1$–C$_4$-alkyl, which is optionally substituted by the radical

R$_2$ and R$_3$ represent H or form a bond, or
R$_1$ and R$_2$ together represent O, —O—CH$_2$—CH$_2$—O— or —S—CH$_2$—CH$_2$—S—,
R$_4$ represents H or the

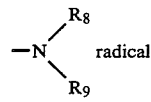 radical or
R$_3$ and R$_4$ represent O, or
R$_1$ and R$_4$ are members of an N-containing six-membered ring and
R$_8$ and R$_9$ represent H or C$_1$–C$_4$-alkyl, or optionally form, with the N atom, a heterocyclic 5-membered or 6-membered ring, which can optionally also contain a further hetero-atom from the series comprising N, O or S,
R$_5$ represents H, C$_1$–C$_4$-alkyl or the group

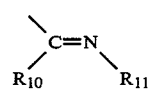

or
R$_5$ and R$_3$ form a bond, and
R$_{10}$ and R$_{11}$ represent C$_1$–C$_4$-alkyl or are members of an N-containing 5-membered or 6-membered ring,
R$_6$ represents H or C$_1$–C$_4$-alkyl and
R$_7$ represents H or halogen or an acid addition salt thereof.

2. A compound or salt according to claim 1, in which
R$_1$ represents H or C$_1$–C$_3$-alkyl, which is substituted by the radical

wherein
R$_8$ and R$_9$ independently of one another represent H or C$_1$–C$_4$-alkyl or, together with the N atom, form a piperidine, pyrrolidone, morpholine or piperazine ring,
R$_4$ and R$_5$ represent H,
R$_2$ and R$_3$ represent H or form a bond,
R$_6$ represents CH$_3$ and
R$_7$ represents H or F.

3. A compound or salt according to claim 1, in which
R$_1$, R$_4$ and R$_5$ represent H,
R$_2$ and R$_3$ represent H or form a bond,
R$_6$ represents CH$_3$ and
R$_7$ represents F.

4. A compound according to claim 1, wherein such compound is 8-methyl-6-(4-fluorophenyl)-6,7,8,9-tetrahydro-1H-pyrido[4,3-g]indole of the formula

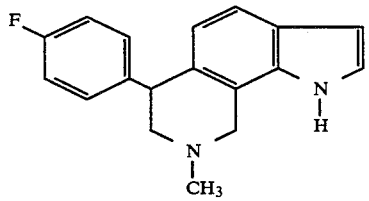

or an acid addition salt thereof.

5. A compound according to claim 1, wherein such compound is 8-methyl-6-(4-fluorophenyl)-2,3,6,7,8,9-hexahydro-1H-pyrido[4,3-g]indole of the formula

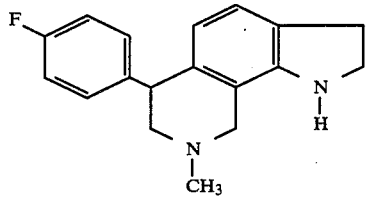

or an acid addition salt thereof.

6. A compound according to claim 1, wherein such compound is 3-(4-morpholinylmethyl)-8-methyl-6-phenyl-6,7,8,9-tetrahydro-1H-pyrido[4,3-g]indole of the formula

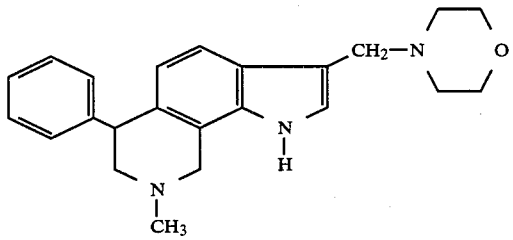

or an acid addition salt thereof.

7. A compound according to claim 1, wherein such compound is 3-(isopropylaminoethyl)-8-methyl-6-phenyl-6,7,8,9-tetrahydro-1H-pyrido[4,3-g]indole of the formula

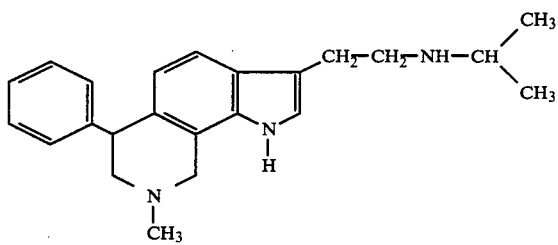

or an acid addition salt thereof.

8. A composition active on the central nervous system comprising a central nervous system-output modifying effective amount of a compound or salt according to claim 1 in admixture with a diluent.

9. A method of modifying the output of the central nervous system which comprises administering to a patient in need thereof a central nervous system-output modifying effective amount of a compound or salt according to claim 1.

10. The method according to claim 10, wherein such compound is
- 8-methyl-6-(4-fluorophenyl)-6,7,8,9-tetrahydro-1H-pyrido[4,3-g]indole,
- 8-methyl-6-(4-fluorophenyl)-2,3,6,7,8,9-hexahydro-1H-pyrido[4,3-g]indole,
- 3-(4-morpholinylmethyl)-8-methyl-6-phenyl-6,7,8,9-tetrahydro-1H-pyrido[4,3-g]indole or
- 3-(isopropylaminoethyl)-8-methyl-6-phenyl-6,7,8,9-tetrahydro-1H-pyrido[4,3-g]indole, or an acid addition salt thereof.

* * * * *

UNITED STATES PATENT AND TRADEMARK OFFICE
CERTIFICATE OF CORRECTION

PATENT NO. : 4,564,613
DATED : January 14, 1986
INVENTOR(S) : Karl-Heinz Boltze, et al.

It is certified that error appears in the above-identified patent and that said Letters Patent is hereby corrected as shown below:

Col. 4, line 20 — End of formula delete "$R^8$" and substitute --$R_8$--

Col. 6, line 5 — End of formula delete "," and substitute --.--

Col. 7, lines 20 and 28 — Beginning of formula delete " " and substitue -- --

Col. 13, line 48 — Correct spelling of "pharmaceutical"

Signed and Sealed this

Thirteenth Day of May 1986

[SEAL]

Attest:

DONALD J. QUIGG

Attesting Officer

Commissioner of Patents and Trademarks